US00PP08596P

United States Patent [19]

Warriner, deceased

[11] Patent Number: Plant 8,596

[45] Date of Patent: Feb. 15, 1994

[54] FLORIBUNDA ROSE PLANT NAMED 'JACDAZ'

[75] Inventor: William A. Warriner, deceased, late of Tustin, Calif., by Alene B. Warriner, legal representative

[73] Assignee: Bear Creek Gardens, Inc., Medford, Oreg.

[21] Appl. No.: 883,192

[22] Filed: May 14, 1992

[51] Int. Cl.[5] ..... A01H 5/00

[52] U.S. Cl. ..... Plt./29

[58] Field of Search ..... Plt. 28, 29

*Primary Examiner*—Howard J. Locker

*Attorney, Agent, or Firm*—Klarquist, Sparkman, Campbell, Leigh and Whinston

[57] ABSTRACT

A floribunda rose having disease resistant dark green leathery foliage, bright red flowers, profusion of blooms, and being easily propagated by softwood or hardwood cuttings or by budding.

1 Drawing Sheet

The present invention relates to a new and distinct variety of rose plant of the Floribunda class which was originated by me by crossing the variety Razzle Dazzle, U.S. Plant Pat. No. 3,995, with an unnamed rose pink seedling.

The primary objective of this breeding was to produce a new rose variety having the bright red flower color and dark green leathery foliage of Razzle Dazzle combined with the heavy flower production and mildew resistant foliage of the rose pink floribunda unnamed seedling. The objective was substantially achieved along with other desirable improvements as evidenced by the following unique combination of characteristics which are outstanding in the new variety and which distinguish it from its parents, as well as from all other varieties of which I am aware:

1. Bright red flower color;
2. Resistance to powdery mildew and rust;
3. Propogates easily from softwood or hardwood cuttings and by budding;
4. Has dark green leathery glossy foliage;
5. Heavy and continuous bloom production.

Asexual reproduction of this new variety by budding and by softwood and hardwood cuttings, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

i Seed parent.—Razzle Dazzle, U.S. Plant Pat. No. 3,995.

*Pollen parent.*—Unnamed variety.

Classification:

*Botanical.*—*Rosa hybrida.*

*Commercial.*—Floribunda.

FLOWER

Observations made from specimens grown in a garden environment in Somis, Calif. from May–August of 1991.

Blooming habit: Continuous.

Bud:

*Size.*—1¼"–1½" when the petals start to unfurl.

*Form.*—Long, pointed ovoid.

*Color.*—When sepals first divide, bud color is Red Group 46A. When half blown, the upper sides of the petals are Red Group 46B; and the lower sides of the petals are Red Group 46B.

*Sepals.*—Color: Green Group 138C. Surface texture: Covered in fine hairs. There are three lightly appendaged sepals. There are two unappendaged sepals with hairy edges.

*Receptacle.*—Color: Green Group 138B. Shape: Apple. Size: Medium, 6/16"×7/16". Surface: Smooth.

*Peduncle.*—Length; Short, 1½" to 2". Surface: Glandular. Color: Bronzy. Strength: Stiff, erect.

Bloom:

Size.—Medium. Average open size is 3½".

*Borne.*—Singly and several together, in flat clusters.

*Stems.*—Medium, 12–16", strong.

*Form.*—When first open: High centered. Permanence: Flattens, outer petal edges curl slightly.

*Petalage.*—Number of petals under normal conditions: 15.

*Color.*—The upper side of the petals is Red Group 46B. The reverse side of the petals is Red Group 46B. The base of the petals has a small bright yellow half moon at the point of attachment. The major color on the upper side is Red Group 46B.

*Variegations.*—No.

*Discoloration.*—No change in general tonality up to and including end of third day. By day 4 or 5 there is some petal darkening.

*Fragrance.*—Slight.

Petals:

*Texture.*—Thick, leathery.

*Shape.*—Notched and deltoid.

*Form.*—Tips slightly recurved.

*Arrangement.*—Imbricated, with few petaloids in the center.

*Persistence.*—Drop off cleanly.

*Lastingness.*—On the plant: Fair, 5 days. As a cut flower: Fair, 5 days.

Reproductive parts:

*Anthers.*—Size: Medium. Quantity: Many. Color: Yellow. Arrangement: Regular around styles, mixed with occassional petaloids.

*Filaments.*—Color: Yellow with a slight touch of pink.

*Pollen.*—Color: Gold yellow.

*Styles.*—Color: Greenish.

*Stigmas.*—Color: Greenish white.

Form: Bush.

Growth: Vigorous; upright; branching.

Foliage:

*Number of leaflets on normal mid-stem leaves.*—5 or 7.

*Size.*—Medium, 5"×3".

*Quantity.*—Abundant.

*Color.*—New foliage: Reddish. Old foliage: Dark Green.

Leaflets:

*Shape.*—Pointed oval.

*Texture.*—Upper side: Leathery, glossy.

*Edge.*—Serrated.

*Serration.*—Single, small.

*Petiole rachis.*—Color: Green.

*Petiole underside.*—Smooth.

*Stipules.*—Long ¾", bearded.

*Disease resistance.*—Resistant to mildew and rust under normal growing conditions at Somis, Calif.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—Short, hooked downward.

*Color when young.*—Red.

Small prickles:

*Quantity.*—On main stalks: None. On laterals: None.

I claim:

1. A new and distinct variety of rose plant of the Floribunda class, substantially as herein shown and described, characterized particularly as to novelty by the unique combination of its disease resistant dark green leathery glossy foliage, its very bright red flower color, its profusion of bloom and its ease of propogation by softwood or hardwood cuttings and by budding.

* * * * *

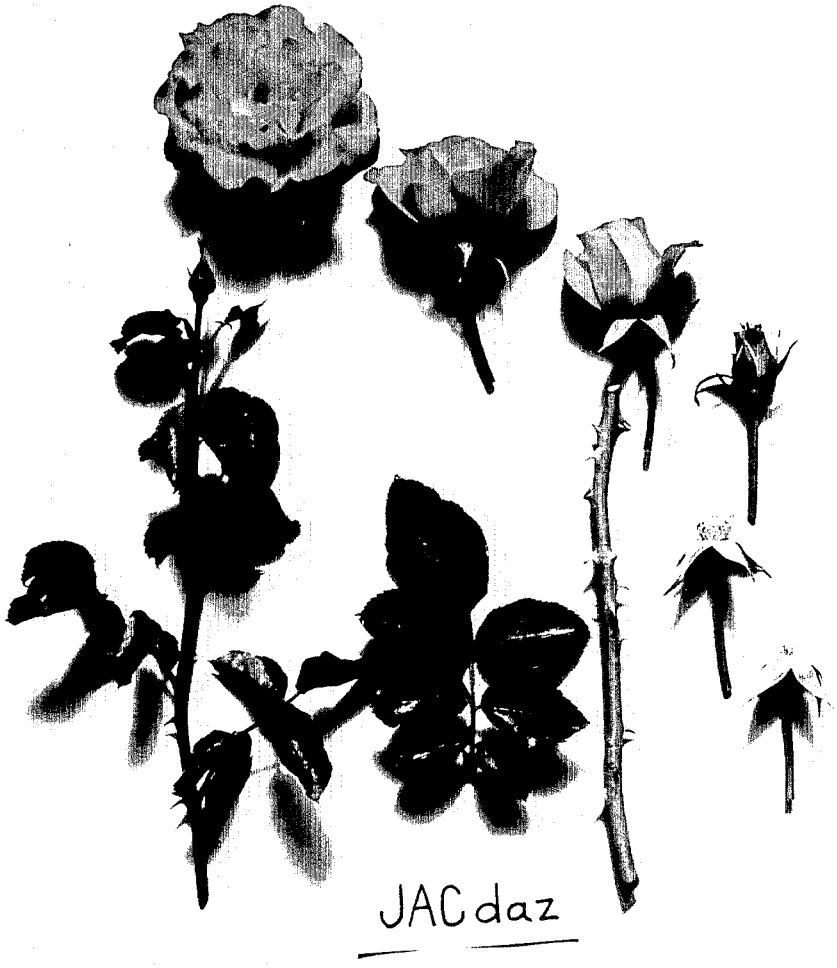
JACdaz